US012811005B2

(12) United States Patent
Kim et al.

(10) Patent No.: US 12,811,005 B2
(45) Date of Patent: Nov. 24, 2026

(54) METHOD FOR DETERMINING USER'S STATE AND APPARATUS PERFORMING THE METHOD

(71) Applicant: KT&G CORPORATION, Daejeon (KR)

(72) Inventors: Jae Hyun Kim, Daejeon (KR); Minseok Jeong, Daejeon (KR); Tae Young Chung, Daejeon (KR)

(73) Assignee: KT&G CORPORATION, Daejeon (KR)

( * ) Notice: Subject to any disclaimer, the term of this patent is extended or adjusted under 35 U.S.C. 154(b) by 191 days.

(21) Appl. No.: 18/271,941

(22) PCT Filed: Mar. 17, 2023

(86) PCT No.: PCT/KR2023/003604
§ 371 (c)(1),
(2) Date: Jul. 12, 2023

(87) PCT Pub. No.: WO2023/229173
PCT Pub. Date: Nov. 30, 2023

(65) Prior Publication Data

US 2024/0387033 A1 Nov. 21, 2024

(30) Foreign Application Priority Data

May 24, 2022 (KR) ........................ 10-2022-0063540

(51) Int. Cl.
*G16H 40/63* (2018.01)

(52) U.S. Cl.
CPC .................................. *G16H 40/63* (2018.01)

(58) Field of Classification Search
CPC ..... A61B 5/0022; A61B 5/6898; A61B 5/082; A61B 5/097; A61B 5/0205; A61B 5/165;
(Continued)

(56) References Cited

U.S. PATENT DOCUMENTS 10,617,148 B2 * 4/2020 Shenkal ................ A61M 15/06
2008/0083409 A1 * 4/2008 Hamaguchi ........... A61M 16/20
128/205.24

(Continued)

FOREIGN PATENT DOCUMENTS

CN 106455716 A 2/2017
CN 106730193 A * 5/2017 ............ A61M 16/08

(Continued)

OTHER PUBLICATIONS

Brown, Christopher J. et al., "Electronic Cigarettes: product characterisation and design considerations", Tob Control; vol. 23, 2014, pp. ii4-ii11.*

(Continued)

*Primary Examiner* — Igor N Borissov
(74) *Attorney, Agent, or Firm* — Sughrue Mion, PLLC

(57) ABSTRACT

According to one example, in order to determine a use's state, biometric information of a user using an electronic device for providing an aerosol may be measured by the electronic device, the biometric information may be received from the electronic device, and a current state of the user may be determined on the basis of the biometric information.

8 Claims, 4 Drawing Sheets

(58) Field of Classification Search
CPC . A61B 5/021; A61B 5/14542; A61B 5/02438; A61B 5/332; G16H 20/13; G16H 40/63; G16H 50/20; A24F 40/51; A24F 40/65; A24F 40/485
USPC .............................................................. 705/2
See application file for complete search history.

(56) References Cited

U.S. PATENT DOCUMENTS

| | | | | |
|---|---|---|---|---|
| 2009/0064997 | A1* | 3/2009 | Li | A61M 15/0091 128/200.23 |
| 2014/0261400 | A1 | 9/2014 | Addington et al. | |
| 2016/0219932 | A1* | 8/2016 | Glaser | A24F 40/485 |
| 2017/0368273 | A1* | 12/2017 | Rubin | A61M 16/0093 |
| 2021/0337881 | A1* | 11/2021 | Mellinger | A61M 15/008 |

FOREIGN PATENT DOCUMENTS

| | | | | |
|---|---|---|---|---|
| GB | 2508520 | A * | 6/2014 | A61M 11/042 |
| JP | 2020500639 | A * | 1/2021 | A61M 11/06 |
| JP | 2021-516540 | A | 7/2021 | |
| JP | 2022-512062 | A | 2/2022 | |
| KR | 10-2018-0057549 | A | 5/2018 | |
| KR | 10-2021-0088574 | A | 7/2021 | |
| KR | 10-2021-0099183 | A | 8/2021 | |
| KR | 10-2309201 | A | 10/2021 | |
| KR | 10-2021-0155287 | A | 12/2021 | |
| KR | 10-2022-0025523 | A | 3/2022 | |
| WO | 2008/133091 | A1 | 11/2008 | |
| WO | 2017/192778 | A1 | 11/2017 | |
| WO | 2021/137139 | A1 | 7/2021 | |

OTHER PUBLICATIONS

International Search Report for PCT/KR2023/003604 dated Jun. 22, 2023.
Extended European Search Report issued Jun. 6, 2024 in European Application No. 23733830.6.
Japanese Office Action dated Jul. 23, 2024 in Application No. 2023-539143.
Office Action dated Feb. 24, 2026, in European Application No. 23 733 830.6.
Office Action dated Mar. 31, 2026, in Chinese Application No. 202380011250.2.

* cited by examiner

METHOD FOR DETERMINING USER'S STATE AND APPARATUS PERFORMING THE METHOD

CROSS REFERENCE TO RELATED APPLICATIONS

This application is a National Stage of International Application No. PCT/KR2023/003604 filed Mar. 17, 2023, claiming priority based on Korean Patent Application No. 10-2022-0063540 filed May 24, 2022.

TECHNICAL FIELD

The following embodiments relate to technology for determining a state of a user, and more specifically, to technology for determining the state of the user based on a biometric substance of the user.

BACKGROUND ART

Recently, various methods of providing an aerosol to a user are being developed. For example, a need for an apparatus for providing an aerosol such as an electronic cigarette and an inhaler is gradually increasing. In addition, as the need for the method increases, various functions that may be used in the apparatus for providing an aerosol are continually being developed.

DISCLOSURE OF THE INVENTION

Technical Goals

An embodiment may provide a method of determining a state of a user.

An embodiment may provide an apparatus for determining a state of a user.

Technical Solutions

A method of determining a state of a user according to an embodiment includes receiving biometric information of the user from an electronic device, the electronic device including at least one biometric sensor configured to measure the biometric information, and determining a current state of the user based on the biometric information, wherein the electronic device is a device configured to provide an aerosol to the user.

The receiving of the biometric information may include receiving the biometric information from a user terminal connected to the electronic device through near-field wireless communication, and the method of determining the state of the user may further include transmitting the determined current state to the user terminal, wherein the user terminal may be configured to notify the user of the current state by outputting the current state.

A first biometric sensor among the at least one biometric sensor may be located in a mouthpiece of the electronic device.

The first biometric sensor may be configured to measure first biometric information by detecting a target substance included in at least one of liquid and gas in an exhalation of the user.

A second biometric sensor among the at least one biometric sensor may be configured to measure second biometric information by measuring an electrocardiogram, a heart rate, or blood oxygen saturation of the user.

The determining of the current state of the user based on the biometric information may include obtaining standard biometric information of the user and determining the current state based on the standard biometric information and the biometric information.

The standard biometric information may be a standard electrocardiogram, a standard heart rate, or standard blood oxygen saturation of the user, wherein the standard electrocardiogram, the standard heart rate, or the standard blood oxygen saturation of the user may be pre-stored.

The biometric information may be biometric information of the user in a state in which the aerosol may be provided.

The electronic device may include a mouthpiece, a reservoir configured to store the aerosol, and a connection path configured to connect the mouthpiece to the reservoir, wherein the reservoir may include a valve of which a state changes based on negative pressure applied by the user, and the aerosol is provided from the reservoir through the connection path as the state of the valve changes.

A first biometric sensor among the at least one biometric sensor may be located in the mouthpiece or the connection path.

A server for determining a state of a user includes a memory configured to store a program to determine the state of the user and a processor configured to perform the program, wherein the processor may be configured to receive biometric information of the user from an electronic device, the electronic device including at least one biometric sensor configured to measure the biometric information, and determine a current state of the user based on the biometric information, wherein the electronic device may be a device configured to provide an aerosol to the user.

The processor may be configured to receive the biometric information from a user terminal connected to the electronic device through near-field wireless communication, determine the current state of the user based on the biometric information, and transmit the determined current state to the user terminal, wherein the user terminal may be configured to notify the user of the current state by outputting the current state.

BEST MODE FOR CARRYING OUT THE INVENTION

Figure 1:
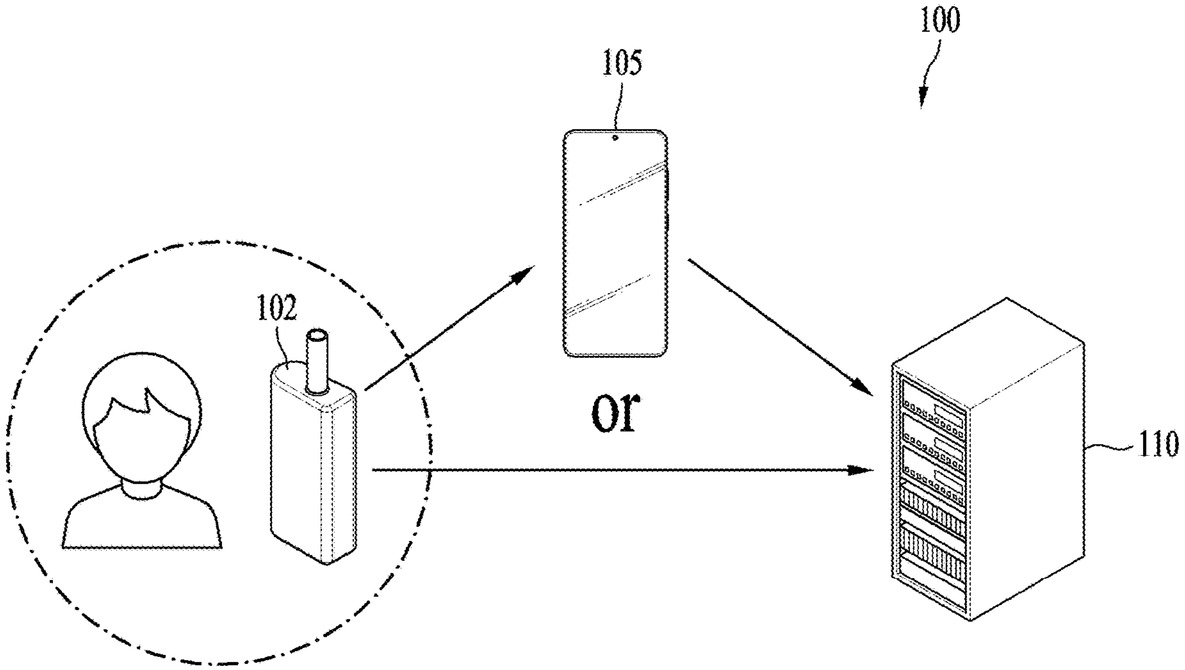
FIG. 1 is a diagram illustrating a system that determines a state of a user, according to an embodiment.

The following structural or functional descriptions of embodiments described herein are merely intended for the purpose of describing the embodiments described herein and may be implemented in various forms. Thus, actual form of implementation is not limited to the embodiments described herein, and should be understood to include all changes, equivalents, and replacements within the idea and the technical scope of the disclosure.

Although terms of "first," "second," and the like are used to explain various components, the components are not limited to such terms. These terms are used only to distinguish one component from another component. For example, a first component may be referred to as a second component, and similarly, the second component may be referred to as the first component within the scope of the present disclosure.

When it is mentioned that one component is "connected" to another component, it may be understood that the one component is directly connected or coupled to another component or still another component is interposed between the two components.

As used herein, the singular forms "a," "an," and "the" are intended to include the plural forms as well, unless the context clearly indicates otherwise. It will be further understood that the terms "include," "comprise," and/or "comprising," when used in this specification, specify the presence of stated features, integers, steps, operations, elements, components or a combination thereof, but do not preclude the presence or addition of one or more other features, integers, steps, operations, elements, components, and/or groups thereof.

Unless otherwise defined herein, all terms used herein including technical or scientific terms have the same meanings as those generally understood by one of ordinary skill in the art. Terms defined in dictionaries generally used should be construed to have meanings matching contextual meanings in the related art and are not to be construed as an ideal or excessively formal meaning unless otherwise defined herein.

Hereinafter, embodiments will be described in detail with reference to the accompanying drawings. When describing the embodiments with reference to the accompanying drawings, like reference numerals refer to like components and a repeated description related thereto will be omitted.

FIG. 1 is a diagram illustrating a system that determines a state of a user, according to an embodiment.

According to an embodiment, a system 100 may include an electronic device 102 and a server 110. For example, the electronic device 102 may be an aerosol-generating apparatus. The electronic device 102 (or the aerosol-generating apparatus) may be referred to as an inhaler apparatus, an electronic cigarette apparatus, or a smoking stick. The electronic device 102 as the aerosol-generating apparatus is described in detail below with reference to FIGS. 2 and 3.

For example, the electronic device 102 may include a communication unit that is capable of performing cellular communications and may be connected to the server 110 through cellular communications.

According to an embodiment, the system 100 may further include a user terminal 105. For example, the user terminal 105 may be a mobile communication terminal or a wearable apparatus. The wearable apparatus may be, for example, a smart watch or smart glasses and is not limited to the described embodiments.

For example, the electronic device 102 and the user terminal 105 may be connected through near-field wireless communication and the electronic device 102 may be connected to the server 110 through the user terminal 105.

A user may be provided with an aerosol generated by the electronic device 102. For example, the aerosol may include substances that include nicotine. In another example, the aerosol may include substances that do not include nicotine. The substances of the aerosol may include water, solvent, ethanol, a plant extract, fragrance, flavoring agent, or vitamin blend. The fragrance may include menthol, peppermint, spearmint oil, various fruit flavored components, and the like but is not limited thereto. The flavoring agent may include an ingredient that may provide various flavors or savors to a user. The vitamin blend may be a mixture of at least one of vitamin A, vitamin B, vitamin C, and vitamin E but is not limited thereto.

According to an embodiment, the electronic device 102 may generate the aerosol using a substance in a cartridge that is inserted in the electronic device 102. The cartridge may be of a gaseous, liquid, or solid type. The cartridge may be a canister. The electronic device 102 using the cartridge may be an inhaler apparatus. A structure of the electronic device 102 as the inhaler apparatus is described in detail below with reference to FIG. 2.

According to another example, the electronic device 102 may generate the aerosol by applying heat to a cigarette or a cartridge inserted in the electronic device 102. For example, the electronic device 102 may generate the aerosol using a substance in a liquid-type cartridge or a solid-type cartridge in the electronic device 102. A method of generating the aerosol by the electronic device 102 may not be limited to the described embodiments. The structure of the electronic device 102 that generates the aerosol by applying heat to the cartridge is described in detail below with reference to FIG. 3.

According to an embodiment, using various sensors included in the electronic device 102, the electronic device 102 may generate sensing information on the electronic device 102 or a user. For example, the sensing information may include biometric information of a user that uses the electronic device 102. The server 110 that received the biometric information from the electronic device 102 may determine information related to a health state of the user based on the biometric information and may provide a service related to health care to the user based on the determined information. In another example, the sensing information may include exercise information of the electronic device 102. A method of determining a state of a user is described in detail below with reference to FIGS. 4 to 6.

Figure 2:
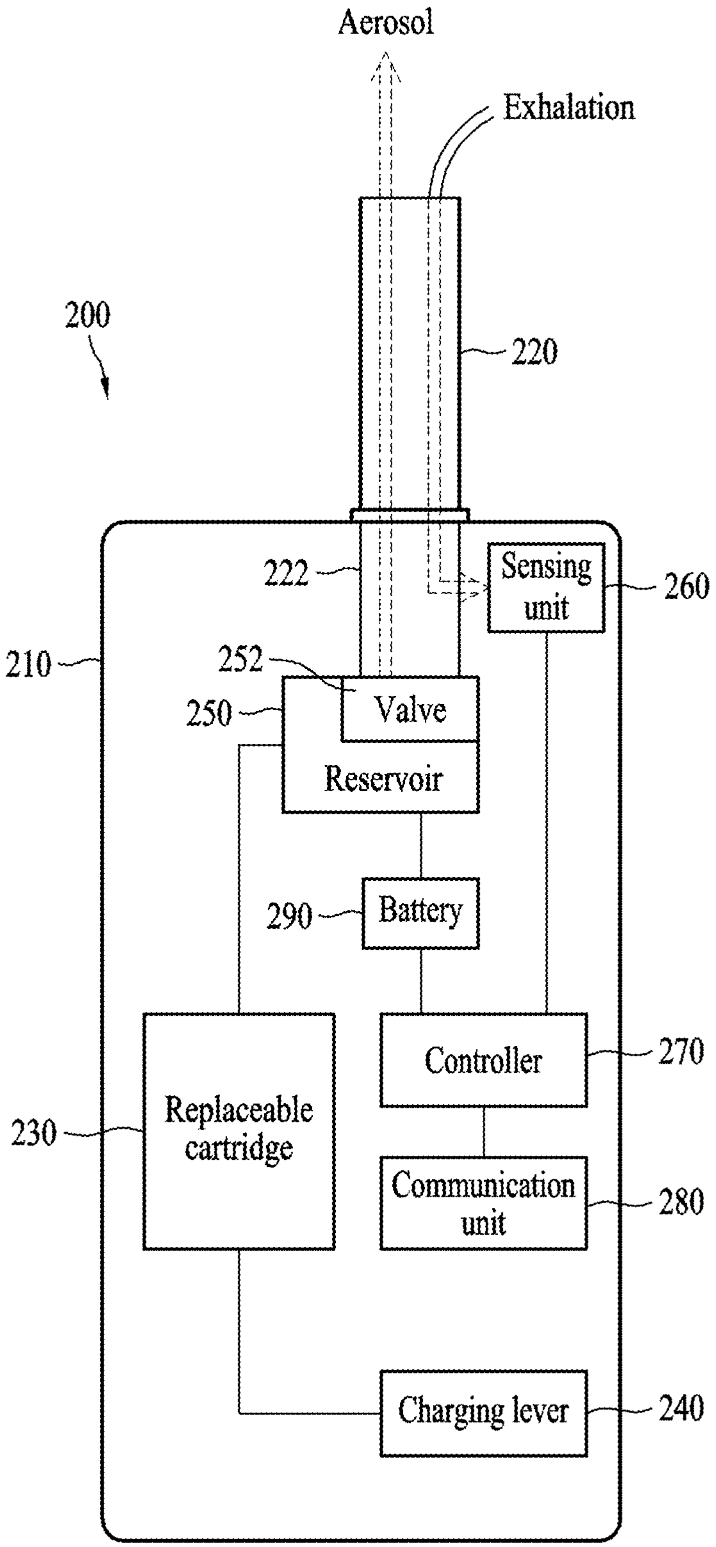
FIG. 2 is a diagram illustrating a configuration of an electronic device according to an embodiment.

FIG. 2 is a diagram illustrating a configuration of an electronic device according to an embodiment.

According to an embodiment, the electronic device 102 described above with reference to FIG. 1 may be of an inhaler apparatus type. For example, an electronic device 200 of the inhaler apparatus type may include a housing 210, a mouthpiece 220, a connecting passage 222, a replaceable cartridge 230, a charging lever 240, a reservoir 250, a sensing unit 260, a controller 270, a communication unit 280, and a battery 290.

The housing 210 may be formed so that the replaceable cartridge 230 may be inserted in the housing 210. For example, the housing 210 may include a transparent portion so that the remaining amount of the cartridge 230 may be shown to the outside. The transparent portion of the housing 210 may be referred to as a sight window.

A user may charge a substance in the cartridge 230 to the reservoir 250 through the charging lever 240. When the user pushes the charging lever 240, the mechanical position of the cartridge 230 may be changed (e.g., pushed upwards) and as the position thereof is changed, the substance in the cartridge 230 may be discharged to the outside. The discharged substance may be stored in the reservoir 250. That is, the reservoir 250 may be charged by the user pushing the charging lever 240. For example, the substance charged in the reservoir 250 may be an amount that the user may inhale about "200" times.

According to an embodiment, the reservoir 250 may include a valve 252. When negative pressure is generated in the connecting passage 222 connected to the reservoir 252, the position of a piston connected to the valve 252 may change according to the strength of the generated negative pressure and the degree of opening of the valve 252 may be adjusted according to the position of the piston. For example, when the user generates negative pressure in the connecting passage 222 through the mouthpiece 220, the valve 252 may be opened due to the generated negative pressure and the substance in the reservoir 250 may be discharged into the connecting passage 222 through the opened valve 252. The substance discharged into the connecting passage 222 may be an aerosol. The user may inhale the aerosol through the connecting passage 222 and the mouthpiece 220. The user may control the amount of the aerosol to be inhaled by adjusting the level of negative pressure. For example, when the user vigorously inhales the mouthpiece 220, the user may inhale a lot of aerosols. When the aerosol is provided to the user in the above manner, droplets generated by an aerosol that is not inhaled may be reduced.

According to an embodiment, the sensing unit 260 may include a first biometric sensor capable of detecting biometric information from a substance excreted from the user. A biometric substance excreted from the user while the user is using the electronic device 200 may flow into the inside of the electronic device 200 (e.g., into the mouthpiece 220 and the connecting passage 222). For example, the biometric substance may include gas and saliva in exhalation. The first biometric sensor capable of detecting the biometric substance may be placed in the electronic device 200 into which the biometric substance may flow. For example, the first biometric sensor may include at least one of a sensor capable of detecting specific gas and a sensor capable of detecting a specific substance in a liquid such as saliva.

According to an embodiment, the sensing unit 260 may further include at least one of a heart rate sensor, a blood pressure sensor, an electrocardiogram sensor, and a blood oxygen saturation sensor as a second biometric sensor. For example, the second biometric sensor may be exposed on the housing 210 or on the outside of the housing 210 to contact with the user's skin. In another example, the second biometric sensor may include a sensor capable of measuring the user's body composition. For example, the body composition may include skeletal muscle mass, basal metabolic rate, body water content, and body fat mass. When the user grabs the electronic device 200, the user's body composition may be measured.

According to an embodiment, the sensing unit 260 may further include a third biometric sensor that is capable of measuring exercise information of the electronic device 200 such as an accelerator sensor and an impact sensor.

According to an embodiment, the controller 270 may control the overall operation of the sensing unit 260 and the communication unit 280, which may be connected to the controller 270. For example, the controller 270 may include at least one processor. The processor may be implemented as an array of multiple logic gates or may be implemented as a combination of a general-purpose microprocessor and a memory in which a program that may be executed by the microprocessor is stored. In addition, one of ordinary skill in the art to which the present embodiment belongs may understand that the processor may also be implemented as other types of hardware.

According to an embodiment, the communication unit 280 may transmit data generated by the electronic device 200 to an external apparatus (e.g., the user terminal 105 and the server 110) through cellular communication and/or near-field wireless communication. The data generated by the electronic device 200 is described in detail below with reference to FIG. 5.

The communication unit 280 may include Bluetooth communication, a Bluetooth Low Energy (BLE) communication unit, a near-field wireless communication unit, a wireless local area network (WLAN), a ZigBee communication unit, an Infrared Data Association (IrDA) communication unit, a Wi-Fi Direct (WFD) communication unit, an ultra-wideband (UWB) communication unit, an ANT+ communication unit, and the like but is not limited thereto.

According to an embodiment, the battery 290 may provide power used for the electronic device 200 to operate. For example, the battery 290 may provide the power needed for the sensing unit 260, the controller 270, and the communication unit 280 to operate. In addition, the battery 290 may provide the power needed for a display, a sensor, a motor, and the like included in the electronic device 200 to operate.

Figure 3:
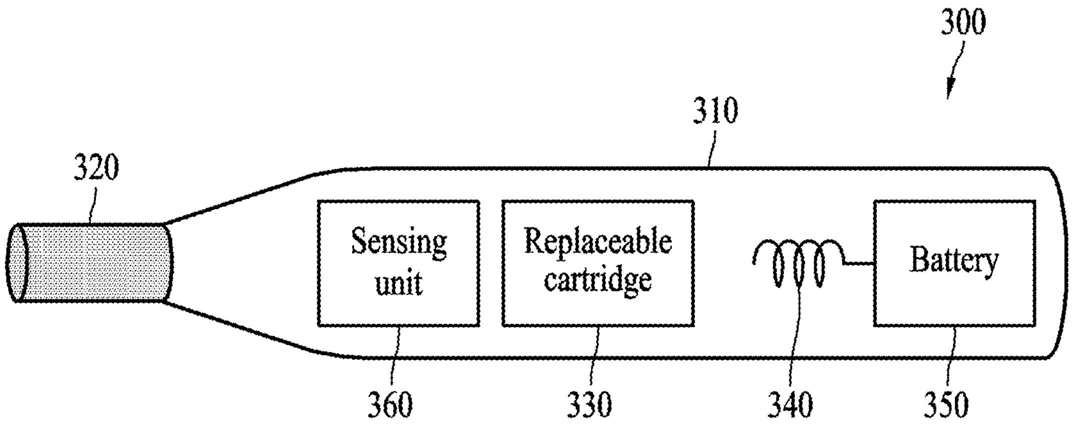
FIG. 3 is a diagram illustrating a configuration of an electronic device according to another embodiment.

FIG. 3 is a diagram illustrating a configuration of an electronic device according to another embodiment.

An electronic device 300 according to an embodiment may include a housing 310, a sensing unit 360, a replaceable cartridge (e.g., a solid-type cartridge or a liquid-type cartridge) 330, a coil 340, a controller (not illustrated), a communication unit (not illustrated), and a battery 350. For example, the coil 340 may generate heat by receiving energy from the battery 350. The cartridge 330 may generate an aerosol using the heat generated by the coil 340. A user may inhale the generated aerosol through a mouthpiece 320 (or a tip portion).

Descriptions on the sensing unit 360, the controller, and the communication unit according to an embodiment may be replaced by the descriptions on the sensing unit 260, the controller 270, and the communication unit 280 described above with reference to FIG. 2.

Figure 4:
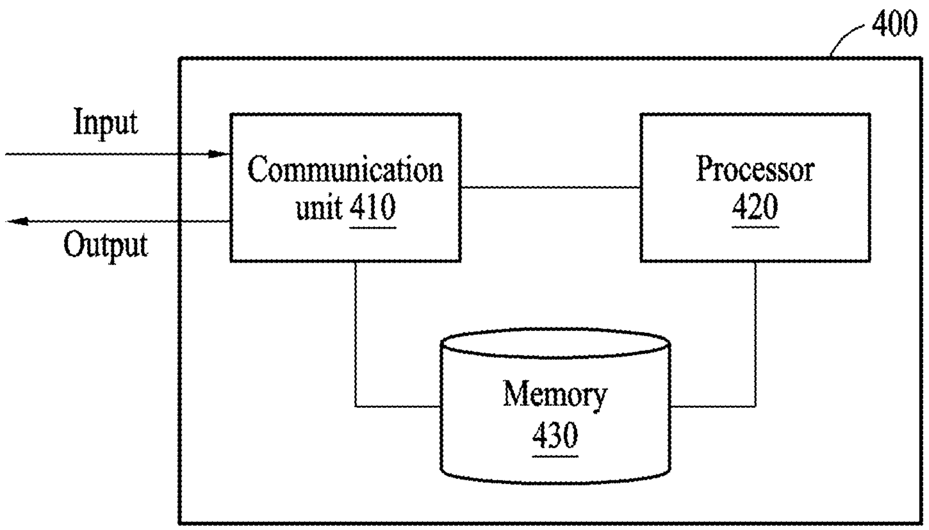
FIG. 4 is a diagram illustrating a configuration of a server according to an embodiment.

FIG. 4 is a diagram illustrating a configuration of a server according to an embodiment.

According to an embodiment, a server 400 may include a communication unit 410, a processor 420, and a memory 430. For example, the server 400 may be the server 110 described above with reference to FIG. 1.

The communication unit 410 may transmit and receive data while being connected to the processor 420 and the memory 430. The communication unit 410 may transmit and receive the data while being connected to another external apparatus. Hereinafter, the term "transmit and receive "A"" may refer to "transmit and receive "information or data that represents A.""

The communication unit 410 may be implemented as circuitry in the server 400. For example, the communication unit 410 may include an internal bus and an external bus. In another example, the communication unit 410 may be a component that connects the server 400 to an external apparatus. The communication unit 410 may be an interface. The communication unit 410 may receive data from the external apparatus and transmit the data to the processor 420 and the memory 430.

The processor 420 may process data that the communication unit 410 received and data stored in the memory 430. A "processor" may be a hardware-implemented data processing device having a circuit with a physical structure for executing desired operations. For example, the desired operations may include code or instructions in a program. For example, the hardware-implemented data processing device may include a microprocessor, a central processing unit (CPU), a processor core, a multi-core processor, a multiprocessor, an application-specific integrated circuit (ASIC), a field programmable gate array (FPGA), and the like.

The processor 420 may execute computer-readable code (e.g., software) stored in a memory (e.g., the memory 430) and instructions induced by the processor 200.

The memory 430 may store data that the communication unit 410 received and data processed by the processor 420. For example, the memory 430 may store a program (or an application, software, etc.). The stored program may be a combination of syntaxes that are coded so that a current state of a user may be determined and that are executable by the processor 420.

According to an aspect, the memory 430 may include at least one volatile memory, non-volatile memory, and random-access memory (RAM), flash memory, a hard disk drive, and an optical disc drive.

The memory 430 may store a set of instructions (e.g., software) for operating the server 400. The set of instructions for operating the server 400 may be executed by the processor 420.

The communication unit 410, the processor 420, and the memory 430 are described in detail below with reference to FIGS. 5 and 6.

Figure 5:
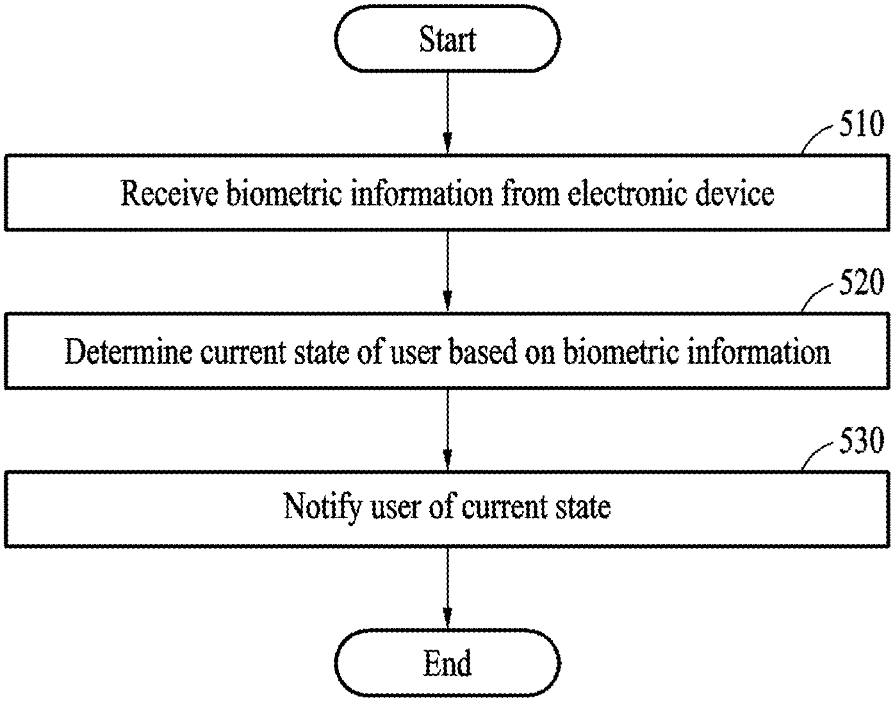
FIG. 5 is a flowchart of a method of determining a state of a user, according to an embodiment.

FIG. 5 is a flowchart of a method of determining a state of a user, according to an embodiment.

Operations 510 to 530 below may be performed by the server 400 that is described above with reference to FIG. 4.

In operation 510, the server 400 may receive biometric information from an electronic device (e.g., the electronic device 102 of FIG. 1, the electronic device 200 of FIG. 2, and the electronic device 300 of FIG. 3). The biometric information may be information generated by the first biometric sensor and/or the second biometric sensor of the sensing unit 260 of FIG. 2 or the sensing unit 360 of FIG. 3.

According to an embodiment, a substance generated when a disease develops or progresses may be a biomarker, and a biometric sensor of the electronic device may detect the biomarker. The detected biomarker may be included in the biometric information.

For example, the biometric information may include whether a specific gas included in a user's exhalation is detected and the concentration of the gas. In another example, the biometric information may be whether a specific substance included in the user's saliva is detected. In another example, the biometric information may further include at least one of a heart rate, blood pressure, an electrocardiogram, and blood oxygen saturation of the user.

According to an embodiment, the server 400 may receive exercise information other than the biometric information from an electronic device. The exercise information may be information generated by the third biometric sensor of the sensing unit 260 of FIG. 2 or the sensing unit 360 of FIG. 3.

According to an embodiment, when an electronic device is not directly connected to the server 400, the electronic device may be connected to the server 400 through a user terminal (e.g., the user terminal 105 of FIG. 1) that is a mobile communication terminal. The user terminal may, through an application installed on the user terminal, receive the biometric information and transmit the received biometric information to the server 400.

In operation 520, the server 400 may determine a current state of the user based on the biometric information.

According to an embodiment, the current state may include whether the user has a specific disease. For example, the specific disease may include an oral disease, a genetic disease, and the like. The genetic disease may include diabetes, dementia, and the like and is not limited to the described embodiments. When detection information of a biomarker that is predetermined for a specific disease is included in the biometric information, the current state of the user may be determined based on the detection information.

According to an embodiment, the current state may be a stress level of the user. For example, the stress level of the user may be determined based on at least one of the heart rate, the blood pressure, the electrocardiogram, and the blood oxygen saturation of the user. A method of determining the current state of the user based on at least one of the heart rate, the blood pressure, the electrocardiogram, and the blood oxygen saturation of the user is described in detail below with reference to FIG. 6.

According to an embodiment, the server 400 may store the history of the user. For example, the history may be stored in association with the current state and a determination time of the user. The user may check their health state through the history.

In operation 530, the server 400 may notify the user of the current state. For example, the server 400 may transmit the determined current state to the electronic device, and the electronic device may notify the user of the current state through a display, a speaker, and a vibration motor. In another example, the server 400 may transmit the determined current state to the user terminal, and the user terminal may output the current state to the user through an application.

According to an embodiment, although operations 510 to 530 above are described with reference to FIG. 4 as being performed by the server 400, when the user terminal has sufficient computing ability, operations corresponding to operations 510 to 530 may also be performed by the user terminal.

According to an embodiment, although operations 510 to 530 above are described with reference to FIG. 4 as being performed by the server 400, when the electronic device has sufficient computing ability, operations corresponding to operations 510 to 530 may also be performed by the electronic device. An operation corresponding to operation 510 may not be performed by the electronic device.

Figure 6:
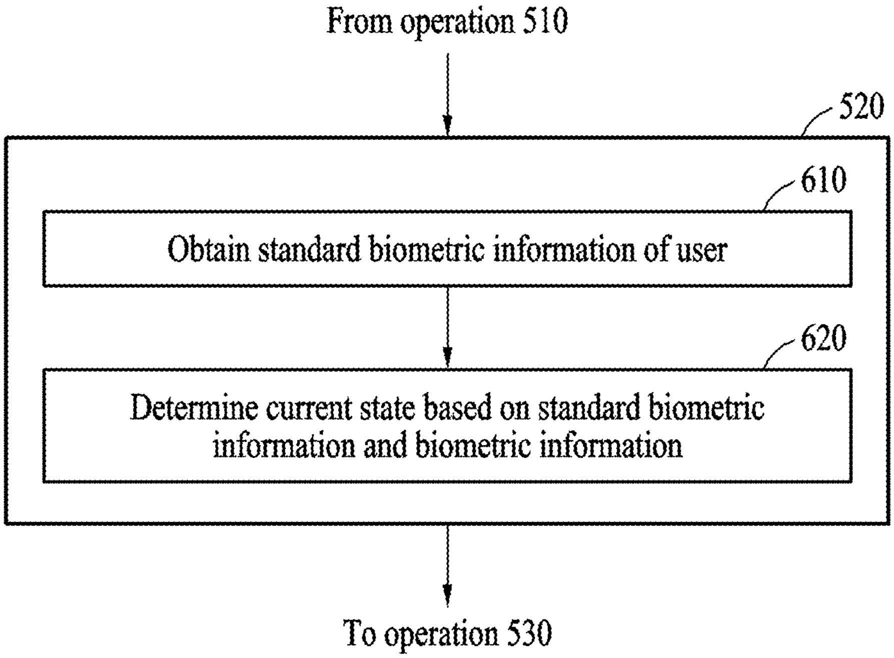
FIG. 6 is a flowchart of a method of determining a current state based on standard biometric information of a user, according to an embodiment.

FIG. 6 is a flowchart of a method of determining a current state based on standard biometric information of a user, according to an embodiment.

According to an embodiment, operation 520 described above with reference to FIG. 5 may include operations 610 and 620 below.

In operation 610, the server 400 may obtain standard biometric information of an identified user. For example, the server 400 may identify the user through an identifier that is transmitted along with the standard biometric information.

For example, the standard biometric information may be information on a standard electrocardiogram, a standard hear rate, and standard blood oxygen saturation of the user. The standard biometric information of the user may be pre-measured by the electronic device and the result may be stored in the server 400. The standard biometric information may be pre-measured in various states of the user. For example, the standard biometric information may be obtained in a state of high stress. In another example, the standard biometric information may be obtained in a state of low stress. In another example, standard biometric information may be obtained in a comfortable state.

In operation 620, the server may determine the current state based on the standard biometric information and the biometric information received from the electronic device. For example, the current state may be determined based on the similarity between the standard biometric information and the biometric information. The determined current state may correspond to the stress level of the user.

The method according to the above-described embodiments may be recorded in non-transitory computer-readable media including program instructions to implement various operations which may be performed by a computer. The media may also include the program instructions, data files, data structures, and the like alone or in combination. The program instructions recorded on the media may be those specially designed and constructed for the purposes of the embodiments, or they may be of the well-known kind and available to those having skill in the computer software arts. Examples of non-transitory computer-readable media include magnetic media such as hard disks, floppy disks, and magnetic tape; optical media such as CD ROM discs and DVDs; magneto-optical media such as floptical disks; and hardware devices that are specially configured to store and perform program instructions, such as read-only memory (ROM), random access memory (RAM), flash memory, and the like. Examples of program instructions include both machine code, such as code produced by a compiler, and higher-level code that may be executed by the computer using an interpreter. The above-described hardware devices may be configured to act as one or more software modules in order to perform the operations of the above-described embodiments, or vice versa.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software may also be distributed over network coupled computer systems so that the software is stored and executed in a distributed fashion. The software and data may be stored by one or more non-transitory computer readable recording media.

While this disclosure includes embodiments illustrated with reference to limited drawings, it will be apparent to one of ordinary skill in the art that various changes in form and details may be made in these embodiments without departing from the spirit and scope of the claims and their equivalents. Descriptions of features or aspects in each embodiment are to be considered as being applicable to similar features or aspects in other embodiments. Suitable results may be achieved if the described techniques are performed in a different order, and/or if components in a described system, architecture, device, or circuit are coupled or combined in a different manner and/or replaced or supplemented by other components or their equivalents.

Therefore, the scope of the disclosure is defined not by the detailed description, but by the claims and their equivalents, and all variations within the scope of the claims and their equivalents are to be construed as being included in the disclosure.

The invention claimed is:

1. An electronic device comprising:

a housing;

a mouthpiece external to the housing;

a reservoir disposed in the housing configured to store an aerosol; and a connection passage in the housing and configured to connect the mouthpiece to the reservoir such that a connection path is formed in which a user inhaling through the mouthpiece causes the aerosol to move from the reservoir through the mouthpiece via the connection path and user exhalation moves from the mouthpiece through the connection passage into the housing via the connection path, a first biometric sensor provided in the housing, the first biometric sensor configured to measure biometric information of the user exhalation that enters the housing via the connection path, wherein the reservoir comprises a valve, and when negative pressure is generated in the connection path based on the user inhaling through the mouthpiece, a position of a piston connected to the valve varies according to a strength of the generated negative pressure, and a degree of opening of the valve is adjusted according to the position of the piston, wherein the aerosol is provided from the reservoir through the connection path as a state of the valve changes, wherein an amount of aerosol to be inhaled by the user is controllable based on a level of the generated negative pressure, and wherein the electronic device is a device configured to provide the aerosol to the user.

2. The electronic device of claim 1, further comprising:

a processor configured to transmit the biometric information to a server.

3. The electronic device of claim 2, further comprising: a second biometric sensor in the mouthpiece of the electronic device.

4. The electronic device of claim 2, wherein the biometric information is biometric information of the user in a state in which the aerosol is provided.

5. The electronic device of claim 3, wherein the first biometric sensor is configured to measure first biometric information by detecting a target substance included in at least one of liquid and gas in the user exhalation.

6. The electronic device of claim 3, wherein a third biometric sensor is configured to measure third biometric information by measuring an electrocardiogram, a heart rate, or blood oxygen saturation of the user.

7. The electronic device of claim 6, wherein the server is configured to:

obtain standard biometric information of the user; and determine a current state of the user based on the standard biometric information and the biometric information.

8. The electronic device of claim 7, wherein the standard biometric information is a standard electrocardiogram, a standard heart rate, or standard blood oxygen saturation of the user, which is pre-stored.

* * * * *